United States Patent [19]

Scholten et al.

[11] Patent Number: 5,143,848
[45] Date of Patent: Sep. 1, 1992

[54] METHOD OF STABILIZING COLOSTRUM FOR IMMUNOCHEMICAL EXAMINATION

[75] Inventors: Rudolf Scholten; Lucas A. T. Hilgers; Marinus W. Weststrate, all of Weesp, Netherlands

[73] Assignee: Duphar International Research B.V., Weesp, Netherlands

[21] Appl. No.: 579,580

[22] Filed: Sep. 10, 1990

[30] Foreign Application Priority Data

Sep. 13, 1989 [NL] Netherlands ............... 8902284

[51] Int. Cl.$^5$ .................. G01N 33/06; G01N 1/00
[52] U.S. Cl. .............................. 436/8; 436/23; 436/176; 422/28; 556/2
[58] Field of Search ............ 436/176, 8, 23; 422/28; 556/2, 57, 118

[56] References Cited

U.S. PATENT DOCUMENTS 3,910,839 10/1975 Tuomarla et al. ............ 514/312 X
4,512,987 4/1985 Schindlery ................... 514/861 X
4,636,476 1/1987 Brunt et al. .................. 436/176 X
4,720,455 1/1988 Babu et al. ................... 435/7.93

OTHER PUBLICATIONS

Schain, Science, 110, pp. 121-122 (1949).

Primary Examiner—James C. Housel
Assistant Examiner—William Chan
Attorney, Agent, or Firm—Stevens, Davis, Miller & Mosher

[57] ABSTRACT

A method of stabilizing a sample of colostrum or milk which is intended for immunochemical examination, by adding a stabilizing system which comprises the following components:
(a) a microbiological preservative,
(b) a buffer solution which buffers the sample at a pH between 5 and 8, preferably between 5.5 and 6.5, and
(c) one or more non-ionic surface-active substances, the components (a), (b) and (c) being selected in such manner that they do not interfere with the immunochemical examination to be carried out. The invention also relates to the stabilization kit to be used for this purpose.

7 Claims, No Drawings

METHOD OF STABILIZING COLOSTRUM FOR IMMUNOCHEMICAL EXAMINATION

The invention relates to a method of stabilizing a sample of colostrum or milk which is intended for immunochemical examination, as well as to a stabilization kit for stabilizing a sample of colostrum or milk.

In veterinary diagnostics the antibody titres against various diseases are usually determined in the blood serum. Taking blood for this purpose should be done by a veterinary surgeon. In a number of cases the same determination may also be carried out in colostrum or milk. The testing of milk has advantages in particular in examinations of cattle on a large scale, because:

(i) a veterinary surgeon is not necessary for taking samples, so that the cost of taking samples and hence the total cost of the immunochemical examination is reduced considerably;

(ii) the taking of the samples causes no or only little stress in the animals, and (iii) in some cases the sensitivity of the determination may even be improved by using colostrum instead of serum; in fact, colostrum comprises a high concentration of antibodies.

However, it has been found in practice that colostrum or milk provides reliable results only when the samples of colostrum or milk to be used for the examination are treated very carefully. Storage at too high temperatures gives rise to unrealiable results; this effect has been found to occur sometimes already after 24 hours. Reliable results are obtained only when the samples are stored carefully at $-20°$ C. In connection with the said sensitivity of colostrum and milk, the samples to be examined have to be collected, stored and transported under carefully controlled conditions. These controlled conditions are difficult to realise in field examinations on a large scale, for example, the eradication programme in pigs as suggested for Aujeszky's disease and in regions or countries having a less suitable infra structure for storage and transport of the samples. As a result of this, the possibility of determining antibody titres in colostrum and milk is impeded.

It is the object of the invention to enable immunochemical examination of samples of colostrum or milk in practice without the reliability of the results obtained being damaged.

According to the present invention this object can be achieved by adding to the sample of colostrum or milk intended for immunochemical examination a stabilizing system in a quantity which is sufficient for stabilization, which system comprises the following components:

(a) a antimicrobial agent, (b) a buffer solution which buffers the sample at a pH between 5 and 8, preferably between 5.5 and 6.5, and (c) one or more non-ionic surface-active substances. The components should be chosen to be so that they do not interfere with the immunochemical examination to be carried out. This means that the components are not allowed, either individually, or in combination with each other, to influence the results of the test or tests to be carried out. A wide range of commercially available detergents may be used in making the choice of the non-ionic surface-active substances to be used.

It has been found that when adding such a stabilizing system the antibody titres, i.e. the concentration of antibodies, in samples of colostrum or milk do not change, not even in prolonged storage at elevated temperature (37° C.), so that immunochemical examination remains possible with reliable results. Upon evaluating the invention it should further be considered that milk is a very special body fluid which imposes high requirements on the additives to be used in general and on the stabilizing system to be used in particular.

For optimum stabilization a mixture of at least two non-ionic surface-active substances at least one of which has an HLB value between 12 and 16 is to be preferred.

As a antimicrobial agent is preferably chosen a dichromate, for example, sodium dichromate, potassium dichromate or ammonium dichromate, or an organic mercury compound, for example, an ethyl mercurithiosalicylate. The stabilizing system, and hence also the buffer solution, is preferably added in a concentrated condition, so that the sample is diluted as little as possible. Such a dilution reduces the sensitivity of the test or tests to be carried out. It has been found that a concentrated buffer solution can be obtained by using as buffer components a weak inorganic acid with the salt derived therefrom.

Best suitable as the last-mentioned component of the stabilizing system has been found to be an aqueous solution of a mixture of at least two non-ionic surface-active substances, comprising a polyoxyethylene sorbitan fatty acid ester, a block copolymer which is built up from polyoxyethylene and polyoxypropylene and which has a comparatively high polyoxyethylene content, and optionally an alkyl phenol polyoxyethylene compound. Polyoxyethylene sorbitan fatty acid esters are marketed, for example, under the trademark Tween ®, for example, Tween 80 and Tween 85. Polyoxyethylene-polyoxypropylene block copolymers are available under the trademark Pluronic ®; a copolymer used in the examples having a comparatively high polyoxypropylene content (approximately 90%) is Pluronic PE 3100. Nonidet ® P-40 is an example of an alkyl phenol polyoxyethylene compound, in which the alkyl group comprises 8 carbon atoms and in which on an average 9 ethyleneoxide molecules per molecule are present.

It is of great advantage when the user, for example, the cattle-breeder, can establish whether the stabilizing system has been added, that is, whether the sample of colostrum or milk has been stabilized. This is of even greater importance for the authority performing the immunochemical examination. In fact, when it can easily be established that the sample has been stabilized, one may be sure that the reliability of the results of the examination is not influenced by the history of the sample of colostrum or milk.

It is an exta aspect of the present invention to make the stabilizing system comprise an indicator with which the sample of colostrum or milk can be coloured. The advantage of the use of dichromate as a preservative is the yellow colouring of a sample of colostrum or milk to which it is added. In an exceptionally favourable formulation the stabilizing system which may be added according to the invention to samples of colostrum or milk therefore comprises a dichromate dissolved in a concentrated buffer solution. In connection with the desired pH-range and the great water solubility, $H_2PO_4^-/HPO_4^{2-}$ buffer having a pH of approximately 6.4 is best suitable. The third component of the stabilizing system, namely the surface-active substance or substances, is then preferably added separately in the form of a concentrated aqueous solution. If this component should be used while dissolved in the dichromate buffer solution, more water as a solvent would be necessary to avoid separation of one of the components. This would cause a greater dilution of the sample of colostrum or milk and therewith have a detrimental influence on the sensitivity of the immunochemical examination to be carried out.

An extra advantage is still achieved by adding to the detergent solution (component c) an indicator which provides a colouration of the colostrum or milk sample with the solution comprising the preservative and the buffer as components. An example of a suitable indicator is methylene blue which, with the orange-coloured dichromate solution, gives the sample of colostrum or milk a green colour. When the solution of detergents is forgotten during stabilizing the sample, then the sample colours yellow, when the solution of preservative and buffer is forgotten, then the solution colours blue. Only a green colour of the sample of colostrum or milk to be examined indicates that stabilization has been carried out completely.

The limits within which the stabilizing system is active are very wide. As will become apparent from the examples an excellent stabilization of the sample of colostrum or milk is obtained already when 1% by volume of the stabilizing system is added; the same results are obtained when 2 and 10% by volume of stabilizing system are added.

The invention also relates to a stabilization kit which may be supplied together with a test kit for carrying out an immunochemical examination in a sample of colostrum or milk, in which the test kit comprises the substances necessary for testing and optionally auxiliary means. Such a stabilization kit will usually comprise instructions for use including a stipulation for stabilizing the sample of colostrum or milk taken for the immunochemical examination, namely that the sample has to be stabilized by the addition of the stabilizing system described hereinbefore as soon as possible after the sample has been taken. A test kit for the determination of antibodies against Aujeszky's disease virus in swine is described in non-prepublished Netherlands patent application no. 8901891 in the name of Applicants. A test kit for the determination of antibodies against the bovine leucose virus in cattle is also known. Such test kits may advantageously be used for immunochemical examination of samples of colostrum or milk from pigs and cattle, respectively, provided that these samples comprise a stabilizing system as described hereinbefore.

The invention will now be described in greater detail with reference to the ensuing specific examples.

EXAMPLE I

Stabilization of swine colostrum for immunochemical examination

The following stabilizing system is used:

| | |
|---|---|
| solution A: | 10% by weight of $K_2Cr_2O_7$; 2.5 M $H_2PO_4^-/HPO_4^{2-}$ buffer, pH = 6.4; obtained by titrating 2.5 M $NaH_2PO_4$-solution with 2.5 M sodium hydroxide solution to the desired pH. |
| solution B: | 1% by weight of Tween ® 80; 1% by weight of Nonidet ® P-40; 1% by weight of Pluronic ® PE 3100; 0.05% by weight of methylene blue. |

Colostrum is collected from four sows right after farrowing. The colostrum is immediately deep-frozen and stored at −20° C. till the beginning of the experiment. Each sample is divided before the experiment starts. The stabilizing system is added in a concentration of 2% to one part, the other part is not treated. The stabilized and untreated colostrum are incubated at 28° C. and 37° C., respectively. The Aujeszky gI antibody titre of these samples is determined on day 0, day 7 and day 35 by means of the Suvaxyn ® gI ELISA.

The results are recorded in table A below in the form of per cent optical density; the negative control is set at 100% according to the instructions for use accompanying the test kit.

TABLE A

Determination of antibody titres against the glycoprotein I of Aujeszky's disease virus in stabilized or nonstabilized swine colostrum after storage at different temperatures

| storage conditions | sample: | | | | | | | |
|---|---|---|---|---|---|---|---|---|
| | 1 | | 2 | | 3 | | 4 | |
| temp./time | o | s | o | s | o | s | o | s |
| 0 days | 80.4 | 83.4 | 105.1 | 99.8 | 45.2 | 50.1 | 8.9 | 9.1 |
| 28° C./7 days | 16.4 | 76.4 | 20.8 | 91.0 | 18.4 | 48.0 | 5.7 | 6.5 |
| 28° C./35 days | 3.6 | 68.4 | 3.5 | * | 4.6 | 49.7 | 3.2 | 5.0 |
| 37° C./7 days | * | 89.2 | * | 98.6 | * | 53.2 | * | 9.3 |
| 37° C./35 days | * | 78.2 | * | 87.6 | * | * | * | 4.2 | colostrum samples of various pigs
o = untreated
s = stabilized
* = not carried out It appears from the above results that the stabilized samples can be stored for 35 days, even at 37° C., without its quality has been deteriorated, i.e. with respect to the usefulness for immunochemical examinations. It also appears that the added stabilizing system has no detrimental influence on the test results. On the contrary, upon storing at 28° C., already within one week untreated colostrum can not longer be used for immunochemical examination, because the samples (samples 1, 2 and 3) are wrongly evaluated positively (≦35% optical density).

EXAMPLE II

Stabilization of swine colostrum for immunochemical examination; comparison of stabilizing systems In the same experiment as in Example I the stabilizing system (S1) described therein is compared with a stabilizing system (S2) in which Nonidet P-40 has been omitted. Final concentration of detergents in the colostrum samples is 0.05%; final concentration of $K_2Cr_2O_7$ is 0.2%; final concentration of $H_2PO_4^-/HPO_4^{2-}$ buffer is 0.05 M.

The results (% optical density) shown in Table B have been obtained after storage of the samples at 37° C. for 48 hours.

TABLE B

Determination of antibody titres against Aujeszky gI in swine colostrom.

| Stabilizing system | Sample | | | |
|---|---|---|---|---|
| | 1 | 2 | 3 | 4 |
| S1 | 105.5 | 94.7 | 116.3 | 100.0 |
| S2 | 103.3 | 99.7 | 112.8 | 99.8 |

So the stabilizing systems do not differ significantly from each other. Still a three-components system is preferred, i.c. a stabilizing system with Nonidet P-40, because it has been found that the most uniform results are obtained therewith.

EXAMPLE III

Stabilization of swine colostrum for immunochemical examination; various concentrations of stabilizing system In an experiment similar to example I the stabilizing system described therein is added in various concentrations, namely 10%, 2% and 1%.

The results (% optical density) recorded in Table C have been obtained after storage at 37° C. for 7 days.

TABLE C

Effect of various concentrations of stabilizer on the Aujeszky gI antibody titre determination in swine colostrum.

| storage term (days) | sample: | | | | | | | | |
|---|---|---|---|---|---|---|---|---|---|
| | 1 | | | 2 | | | 3 | | |
| | conc. stab. % | | | | | | | | |
| | 10 | 2 | 1 | 10 | 2 | 1 | 10 | 2 | 1 |
| 0 | 19.2 | 17.9 | 22.4 | 37.3 | 38.3 | 43.1 | 59.8 | 60.7 | 65.2 |
| 7 | 18.4 | 21.3 | 22.3 | 39.7 | 38.6 | * | 60.0 | 58.2 | 59.2 |

*not carried out

So the stabilizing system gives a good stabilization of the colostrum samples in all the concentrations used, namely 10%, 2% and 1%.

EXAMPLE IV

Determination of the Aujeszky gI status in swine colostrum, collected under practical conditions In two pig farms colostrum was collected from each sow after farrowing as a part of normal management. The sample is divided into two parts; one part is stored at −20° C. and transported to the laboratory in the frozen condition, the other part is stabilized with the stabilizing system described in Example I. After adding the stabilizing system (approximately 2%) to the colostrum, the sample is stored at approximately 4° C. No special precautions as regards transport time and storage temperature are taken during transporting said samples to the laboratory. The Aujeszky gI antibody titre is determined in the laboratory with the Suvaxyn ® gI ELISA of both the untreated, frozen samples and of the stabilized samples. The results of this comparative test are recorded in Table D.

TABLE D

Determination of the Aujeszky gI titre of stabilized swine colostrum collected under practical conditions, compared with frozen, untreated samples.

| samples | storage time (days) | Treatment of samples | |
|---|---|---|---|
| | | frozen | stabilized |
| Storage in farm A | | | |
| 1 | 3 | 66.5 | 68.8 |
| 2 | 5 | 8.7 | 8.7 |
| 3 | 14 | 9.1 | 9.6 |
| 4 | 18 | 67.2 | 65.6 |
| 5 | 19 | 57.5 | 49.9 |
| 6 | 25 | 3.3 | 2.8 |
| 7 | 25 | 3.0 | 2.9 |
| 8 | 26 | 2.8 | 2.5 |
| 9 | 28 | 5.4 | 5.1 |
| 10 | 30 | 20.6 | 20.6 |
| 11 | 31 | 5.4 | 4.2 |
| 12 | 34 | 2.8 | 3.1 |
| Storage in farm B | | | |
| 13 | 2 | 8.9 | 9.1 |
| 14 | 3 | 66.7 | 64.5 |
| 15 | 5 | 45.2 | 50.1 |
| 16 | 6 | 105.1 | 99.8 |
| 17 | 6 | 80.4 | 83.8 |
| 18 | 9 | 50.8 | 46.6 |
| 19 | 11 | 3.9 | 5.0 |
| 20 | 12 | 57.2 | 51.8 |
| 21 | 12 | 84.4 | 88.3 |
| 22 | 13 | 98.7 | 88.3 |
| 23 | 19 | 3.3 | 3.0 |
| 24 | 19 | 2.8 | 3.0 |
| 25 | 31 | 3.1 | 3.0 |
| 26 | 33 | 58.4 | 57.9 |
| 27 | 35 | 60.4 | 51.8 |

So by stabilizing the samples, they can be stored and transported under normal practical conditions. After that, the stabilized samples have remained equally well useful for immunochemical examination as the untreated samples which are stored carefully at −20° C. This means that the results of the tests carried out with stabilized samples are so reliable that errors as regards the Aujeszky gI status of the individual animals are excluded.

EXAMPLE V

Stabilization of cow milk for immunochemical examination

The mixed cow-milk samples used for this experiment are stored at −20° C. until the beginning of the test. Before the test each sample is divided. Stabilizing system (2%) is added to one part of the milk, the other part remains untreated. The stabilizing system described in Example I is used. The stabilized and the untreated milk are incubated at 4° C. and 37° C., respectively. Of these samples the bovine leucose virus (BLV) antibody titre is determined on the days indicated in the table below with the BLV-milk ELISA.

The results (% optical density) are recorded in Table E.

TABLE E

Determination of antibody titres against the p24 of BLV in stabilized and unstabilized cow milk after storage at various temperatures.

| storage conditions temp./time | mixed sample: | | | | | |
|---|---|---|---|---|---|---|
| | 1 | | 2 | | 3 | |
| | o | s | o | s | o | s |
| 0 days | 34.1 | 37.1 | 24.8 | 20.9 | 8.0 | 10.2 |
| 4° C./7 days | 33.0 | 34.5 | 26.7 | 21.4 | 9.9 | 9.9 |
| 4° C./35 days | 60.6 | 34.5 | 30.7 | 24.3 | 38.7 | 12.0 |
| 37° C./7 days | decomp. | 34.4 | decomp. | 22.5 | decomp. | 11.3 | o = untreated
s = stabilized
decomp. = milk is spoiled, no longer useful.

It appears from the above results that, in contrast with unstabilized milk, stabilized cow milk is still useful for immunochemical examination after storing for a considerable period of time, because the results of the examination have not changed as compared with day 0 (the beginning of the test).

EXAMPLE VI

Stabilization of colostrum for immunochemical examination; field trials

Trial I: From an Aujeszki negative breeding herd, all sows are colostrum sampled just after farrowing. The colostrum samples of 181 sows are stabilized by the stabilizing system (S1) described in Example I and tested on gI antibodies with the Suvaxyn gI test. None are positive, five samples are dubious and 176 are negative. The dubious samples are retested after defatting the colostrum and the colostrum sera obtained are negative. The results are schematically represented in the Figure below.

Trial II: At several pig breeding farms, colostrum samples are taken from sows after farrowing. The samples are stabilized by stabilizing system (S1) described in Example I and tested in the Suvaxyn gI test. Ninety eight of the 261 samples are positive, 146 negative and 17 samples are dubious. The anti-gI antibody titer both in defatted colostrum and in serum of the positive and dubious animals are measured. Out of the 98 colostrum positive animals 75 react positively and 23 negatively in serum. The latter have low titer in defatted colostrum (>1/16). All dubiously reacting animals are negative in serum and 8 out 17 give dubious results in defatted colostrum. The results are schematically represented in the Figure below.

Conclusions: From the above-described trials it can be concluded that the stabilizing system used eliminates false positive reactions in colostrum. Dubious samples should be further examined after defatting the colostrum. The determination of gI antibodies in colostrum is at least as sensitive as the determination in serum.

Schematic representation of the results of two field trials.

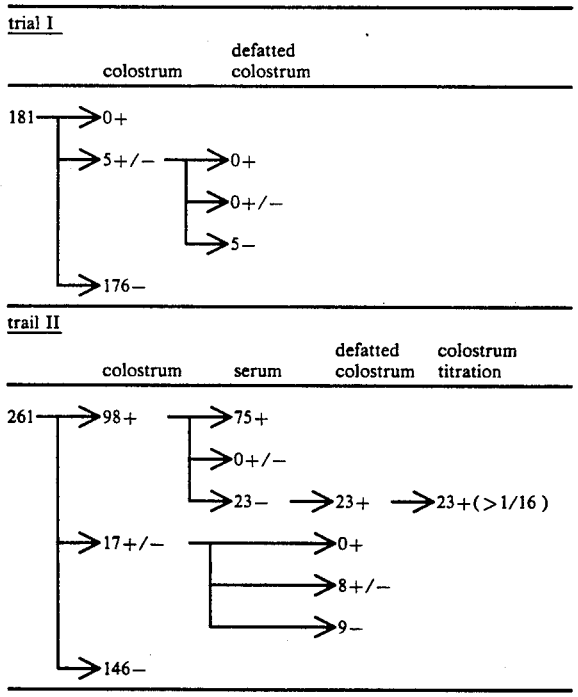

We claim:

1. A stabilization kit to be used for stabilizing a sample of colostrum or milk which is intended for immunochemical examination, characterised in that the kit comprises a stabilizing system comprising the following components:
   (a) an antimicrobial agent,
   (b) a buffer solution which is capable of buffering the sample to be examined at a pH between 5 and 8, and
   (c) at least two non-ionic surface-active substances, and that the kit may further comprise instructions for use, stipulating that the sample of colostrum or milk taken for the immunochemical examination must be stabilized by adding said stabilizing system as soon as possible after taking the sample.

2. A kit as claimed in claim 1, characterised in that it comprises a stabilizing system of which component (c) comprises a mixture of at least two non-ionic surface-active substances at least one of which has an HLB value between 12 and 16.

3. A kit as claimed in claim 2, characterised in that it comprises a stabilizing system having the following components:
   (a) an antimicrobial agent selected from the group consisting of a dichromate and an organic mercury compound,
   (b) a concentrated buffer solution of a weak inorganic acid with the salt derived therefrom, and
   (c) a mixture of at least two non-ionic surface-active substances at least one of which has an HLB value between 12 and 16.

4. The kit as claimed in claim 1, wherein said buffer solution is capable of buffering the sample to be examined at a pH between 5.5 and 6.5

5. A kit as claimed in claim 1 or 2 or 3 or 4, characterised in that it comprises a stabilizing system, of which component (c) consists of an aqueous solution of a mixture of at least two non-ionic surface-active substances, said mixture comprising a polyoxyethylene sorbitan fatty acid ester, a block copolymer which is built up from polyoxyethylene and polyoxypropylene and which has a comparatively high polyoxypropylene content, and optionally an alkyl phenol polyoxyethylene compound.

6. A kit as claimed in claim 5, characterised in that it comprises a stabilizing system having the following components:
   (a) a dichromate, as a preservative, in (b) a concentrated aqueous solution of a $H_2PO_4^-/HPO_4^{2-}$-buffer having a pH of approximately 6.4, and
   (c) an aqueous solution of a mixture of at least two non-ionic surface-active substances, said mixture comprising a polyoxyethylene sorbitan fatty acid ester, a block copolymer which is built up from polyoxyethylene and polyoxypropylene and which has a comparatively high polyoxypropylene content, and optionally an alkyl phenol polyoxyethylene compound.

7. A kit as claimed in claim 6, further characterised in that the solution of surface-active substances further comprises an indicator which provides a colouration of the sample.

* * * * *